United States Patent
Mattison et al.

(10) Patent No.: US 6,586,632 B2
(45) Date of Patent: Jul. 1, 2003

(54) PREPARATION OF QUATERNARY AMMONIUM COMPOUNDS

(75) Inventors: Phillip L. Mattison, Cincinnati, OH (US); Patrick M. McCurry, Jr., West Chester, OH (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 10/102,579

(22) Filed: Mar. 20, 2002

(65) Prior Publication Data

US 2003/0065037 A1 Apr. 3, 2003

Related U.S. Application Data

(60) Provisional application No. 60/279,372, filed on Mar. 28, 2001.

(51) Int. Cl.$^7$ .................. C07C 209/12; C07C 211/63
(52) U.S. Cl. ........................................ 564/296; 564/291
(58) Field of Search ................................ 564/291, 296

(56) References Cited

U.S. PATENT DOCUMENTS

| | | | |
|---|---|---|---|
| 3,190,919 A | | 6/1965 | Swanson |
| 3,816,533 A | * | 6/1974 | Brandstrom et al. . 260/567.6 M |
| 5,308,363 A | * | 5/1994 | Liebermann et al. ..... 23/295 R |
| 5,705,696 A | | 1/1998 | King, Jr. |

* cited by examiner

Primary Examiner—Brian Davis
(74) Attorney, Agent, or Firm—John E. Drach

(57) ABSTRACT

Quaternary ammonium dihydrogen phosphate or bisulfate salts are made by a process comprising the steps of: (1) forming a first mixture by contacting a quaternary ammonium halide with: (a) a water-insoluble organic solvent capable of forming a ternary azeotrope with water and hydrogen halide and (b) an amount of water and sulfuric acid or phosphoric acid sufficient to maintain the temperature of the first mixture in the range of from about 98° C. to about 105° C. when heated; (2) heating the first mixture to a temperature sufficient to separate a ternary azeotrope comprised of hydrogen halide, water and the water-insoluble organic solvent from the first mixture to form a second mixture comprised of water, sulfuric acid or phosphoric acid, the water-insoluble organic solvent and a quaternary ammonium dihydrogen phosphate or bisulfate salt. The process is less time-consuming, less labor intensive, and utilizes relatively small amounts of materials thereby resulting in cost and effluent disposal savings when compared to known methods.

11 Claims, No Drawings

PREPARATION OF QUATERNARY AMMONIUM COMPOUNDS

CROSS-REFERENCE TO RELATED APPLICATIONS

This application claims the benefit of copending provisional application serial No. 60/279,372, filed on Mar. 28, 2001, the entire contents of which are incorporated herein by reference.

STATEMENT REGARDING FEDERALLY SPONSORED RESEARCH OR DEVELOPMENT

Not applicable.

BACKGROUND OF THE INVENTION

Tetraalkyl ammonium halide salts can be used as phase transfer catalysts. An example of such a compound is ALIQUAT® 336 quaternary ammonium compound, a methyl tri-alkylammonium chloride, wherein the alkyl groups are a mixture of C8 and C10 groups. Phase transfer catalysts (PTC) convey anions into an organic reaction phase at a higher concentration and activity than would be the case without the PTC. In functioning as a PTC, the chloride must exchange for the desired anion, which is not always a favored equilibrium. If the anion on the PTC reagent is other than chloride such as phosphate or bisulfate, it will more readily exchange for other anions, resulting in a more efficient catalytic effect. In addition, other quaternary ammonium salts such as hydroxide, carbonate, nitrate, chromate, dichromate, vanadate and tungstate are useful for other applications such as in hydrometallurgical extraction processes or as reagents in chemical processes, but are difficult to prepare by normal methods.

There are several known methods for converting quaternary ammonium chlorides such as ALIQUAT® 336, a methyl trialkylammonium chloride, to quaternary ammonium salts having anions other than chloride but each has its disadvantages. For example, to convert a quaternary ammonium chloride to a quaternary ammonium bisulfate, an organic solution of a quaternary ammonium chloride salt can be contacted with a sequence of aqueous solutions of sodium bisulfate or sulfuric acid, but because the equilibrium is unfavorable, a large excess of the aqueous solution is required in an extended series of contacts to reach a low level of chloride. The chloride salt can also be reacted with dimethyl sulfate to produce methyl chloride and the methylsulfate quaternary ammonium salt, which is subsequently hydrolyzed to the bisulfate and methanol, but this is expensive and involves highly carcinogenic materials. The chloride salt, usually in a diluent to reduce viscosity, can be heated with solid sodium bisulfate, to precipitate the less-soluble sodium chloride, but this requires repetitive equilibrations with excess sodium bisulfate and difficult filtrations. At least four repetitions are needed to reduce the chloride level by 90%. In addition, this method tends to produce significant concentrations of free sulfuric acid in the quaternary ammonium phase. A method that would allow rapid conversion of the chloride to another anion such as the dihydrogen phosphate or bisulfate with easily operated equipment would be desired to allow economic manufacture.

BRIEF SUMMARY OF THE INVENTION

One aspect of the present invention pertains to a process for making a quaternary ammonium dihydrogen phosphate or bisulfate salt comprising the steps of: (1) forming a first mixture by contacting a quaternary ammonium halide with: (a) a water-insoluble organic solvent capable of forming a ternary azeotrope with water and hydrogen halide and (b) an amount of water and sulfuric acid or phosphoric acid sufficient to maintain the temperature of the first mixture in the range of from about 98° C. to about 105° C. when heated; (2) heating the first mixture to a temperature sufficient to separate a ternary azeotrope comprised of hydrogen halide, water and the water-insoluble organic solvent from the first mixture to form a second mixture comprised of water, sulfuric acid or phosphoric acid, the water-insoluble organic solvent and a quaternary ammonium dihydrogen phosphate or bisulfate salt.

The quaternary ammonium dihydrogen phosphate or bisulfate salts can be used as phase transfer catalysts themselves or be readily converted to quaternary ammonium salts having anions not readily obtainable from the chloride salts such as the hydroxide, carbonate, nitrate, chromate, dichromate, vanadate, and tungstate salts. These salts are useful as phase transfer catalysts or as extractants for metals from aqueous solutions in hydrometallurgical metal recovery applications.

Another aspect of the present invention pertains to a liquid quaternary ammonium dihydrogen phosphate or bisulfate salt having a chloride impurity content of less than about one mole percent. Such liquids are practically insoluble in water and are completely soluble in an organic phase of a phase transfer reaction.

Still another aspect of the invention pertains to a process for making quaternary ammonium compounds wherein the anion, G, is other than bisulfate or dihydrogen phosphate wherein G is selected from the group consisting of hydroxide, carbonate, nitrate, chromate, dichromate, vanadate and tungstate.

BRIEF DESCRIPTION OF THE SEVERAL VIEWS OF THE DRAWING

Not applicable

DETAILED DESCRIPTION OF THE INVENTION

One aspect of the present invention pertains to a process for making any quaternary ammonium bisulfate or dihydrogen phosphate salt of the general formula $QHSO_4$ or $QH_2PO_4$ wherein Q is $R_1 R_2 R_3 R_4 N^+$ and wherein each of $R_1 R_2 R_3 R_4$ is independently an alkyl or cycloalkyl group having from 1 to 22 carbon atoms from any quaternary ammonium halide salt, QX, wherein Q is defined above and X is the anion of a distillable acid such as $F^-$, $Cl^-$, $Br^-$ or $I^-$. The term distillable acid is defined as any Bronsted (hydrogen donating) acid which is capable of being vaporized and recondensed without degradation, either by itself or as an azeotrope. Examples include but are not limited to the hydrogen halides as well as most carboxylic acids.

The process according to the invention is based on the reaction of a quaternary ammonium halide in general or a quaternary ammonium chloride in particular with either sulfuric acid or phosphoric acid to produce a quaternary ammonium bisulfate or a quaternary ammonium dihydrogen phosphate and a hydrogen halide. While not wishing to be bound by theory, it is believed that the reaction is thermodynamically unfavored, but can be displaced by removal of the hydrogen halide via distillation of the hydrogen halide azeotrope with water and any solvent that forms a ternary azeotrope with a hydrogen halide and water such as benzene, toluene, heptane or octane when the excess sulfuric acid or phosphoric acid concentration is elevated and the water level in the mixture is low. There appears to be a relationship between the two; higher excess sulfuric acid allows more water to be present in the reaction and still gives good rates of hydrogen halide removal. Since the distillation removes water from the reaction, the desired level of water must be maintained by continuous or periodic addition of fresh water. When operating at atmospheric pressure, the amount of water is any amount of water and sulfuric acid sufficient to maintain the temperature of the reaction mixture in the range of from about 98° C. to about 105° C., preferably from about 102° C. to about 103° C. Alternatively, the reaction could be run by injecting steam into a mixture of the ammonium compound, organic solvent and sulfuric acid with a level of water present.

Any water-insoluble organic solvent capable of forming a ternary azeotrope with water and a hydrogen halide can be used. Toluene is a preferred solvent because it boils high enough to form an azeotrope with a substantial level of hydrogen halide, particularly HCl, but not so high that degradation of the product becomes excessive. Other such solvents that can be used include, but are not limited to, benzene, heptane and octane. While the process according to the invention can be carried out at any pressure, atmospheric pressure is preferred because of the corrosive nature of the distillate.

The process according to the invention can be used for making any quaternary ammonium compound of the formula $QHSO_4$ or $QH_2PO_4$ wherein Q is $R_1 R_2 R_3 R_4N^+$ and wherein each of $R_1 R_2 R_3 R_4$ is independently an alkyl, or group having from 1 to about 22 carbon atoms from any quaternary ammonium halide salt.

The process according to the invention is particularly applicable to the preparation of methyl tri-alkylammonium salts but can be employed to make other quaternary ammonium compounds such as tetrabutyl and methyl tributyl ammonium salts.

The process according to the invention removes an equivalent amount of chloride but with the following advantages over known methods such as those of the comparative examples: less time-consuming; less labor intensive; requires smaller amounts of reagents to drive the exchange thereby resulting in cost and effluent disposal savings.

Another aspect of the present invention is a process according to the invention is a process for making quaternary ammonium salts of the formula

QG wherein Q is defined as above and G is selected from the group consisting of hydroxide, carbonate, nitrate, chromate, dichromate, vanadate and tungstate. The process is comprised of the steps of (1) forming a first mixture by contacting a quaternary ammonium halide with: (a) a water-insoluble organic solvent capable of forming a ternary azeotrope with water and hydrogen halide and (b) an amount of water and sulfuric acid or phosphoric acid sufficient to maintain the temperature of the first mixture in the range of from about 98° C. to about 105° C. when heated; (2) heating the first mixture to a temperature sufficient to separate a ternary azeotrope comprised of hydrogen halide, water and the water-insoluble organic solvent from the first mixture to form a second mixture comprised of water, sulfuric acid or phosphoric acid, the water-insoluble organic solvent and a quaternary ammonium dihydrogen phosphate or bisulfate salt; (3) reacting the quaternary ammonium dihydrogen phosphate or bisulfate salt with an aqueous solution of a salt of anion G.

The following examples are meant to illustrate but not to limit the invention.

EXAMPLE 1

Into a one-liter round bottom flask equipped with mechanical stirrer, thermometer, dropping funnel and Dean-Stark trap with a condenser was added 442 g (0.88 mole at 88% purity) of ALIQUAT® 336 quaternary ammonium salt, 160 g toluene and 215 ml of 808 g/l aqueous $H_2SO_4$ (1.78 mole). The mixture was heated to reflux with stirring. Aliquots of 20 ml of aqueous were withdrawn from the trap and titrated for acid content. At the same time, 20 ml portions of water were added to the reaction to maintain the water level in the reaction. At times, no water was added, thus reducing the water level and accelerating the rate of HCl removal. Over the course of 19 aliquots, the water level in the reaction was reduced by 90 ml, with the temperature rising from 98° to 102° C. The concentration of acid in the distilled aqueous fell over the distillation from 5.3 to 0.12 milliequivalents per gram. The reaction was then cooled, washed with two 250 ml portions of water, and the solvent and residual water were stripped under vacuum producing 492 gm of product containing 0.60 mg chloride per gram of sample, equivalent to over 99% removal.

EXAMPLE 2

To a five-liter round bottomed flask equipped with mechanical stirrer, dropping funnel, thermometer, and Dean-Stark trap with condenser was added 2.5 kg ALIQUAT® 336 quaternary ammonium salt, 0.7 kg toluene and 800 ml of 800 g/l aqueous sulfuric acid. The mixture was heated to reflux while stirring vigorously. As aqueous hydrochloric acid was removed from the trap, additional 880 g/l sulfuric acid was added until the total added was 1.215 liters. The reaction temperature rose from 99° C. to 102° C., at which point water was added to maintain the temperature at 102° C. The initial HCl concentration in the trap of 3.8 N decreased over 22 hours to 0.07 N. After cooling to 50° C., the mixture was washed twice with 1.4 liters each of water. The toluene was then removed under vacuum on a Rotovap, yielding 2.67 kg of product. To avoid solidification upon cooling, 80 g water was added and dissolved. Analysis indicated the product contained 220 mg chloride per kg, equivalent to 0.27% quaternary ammonium chloride. The Acid Value of the product was 99.

Comparative Example

Precipitation Route

In a 3 liter round-bottom flask equipped with stirrer, thermometer and condenser was added 704 g ALIQUAT® 336 (methyltrialkyl($C_{8/10}$)ammonium chloride, 1.4 mole) and 200 ml toluene. The solution was heated with stirring to 80° C., and 285 g (2.4 mole) sodium bisulfate was added over 30 min. The mixture was stirred at 80° C. an additional 6 hours, after which the hot mixture was suction filtered through a coarse scintered glass funnel. The filter cake was washed with 100 ml toluene. The chloride content had been reduced from about 80 mg/g to 21 mg/g. The filtrate was returned to the flask, heated to 80° C., and 100 g fresh sodium bisulfate (0.8 mole) was added over 70 min. After an additional 3.5 hours stirring, the mixture was suction filtered hot, and the cake rinsed with 50 ml toluene. Analysis indicated the filtrate contained 17 mg/g of chloride. The filtrate was returned to the flask, heated to 80° C., and another 100 g sodium bisulfate was added over 50 min. After 2.75 hours stirring, the mixture was filtered hot and the cake washed with 50 ml toluene. The filtrate contained 13 mg/g chloride. The filtrate was returned for a fourth contact with sodium bisulfate (100 g), and filtered hot after 2.75 hours stirring. The filtrate was stripped of toluene under vacuum, giving 699 g of residue containing 2.4 mg/g chloride, equivalent to 96.9% removal.

Comparative Example

Washing Route

ALIQUAT® 336 (158 g) was mixed with 100 ml toluene, and the solution was washed ten times with 100 ml portions of 900 g/L sulfuric acid. Aliquots of the organic phase were taken at various points during the washing, stripped of solvent and analyzed for chloride.

Results are as follows:

| Washes | % Chloride | Relative % Chloride Remaining |
|---|---|---|
| 0 | 7.8 | 100 |
| 1 | 2.35 | 29 |
| 2 | 1.53 | 19 |
| 4 | 1.15 | 14 |
| 7 | 0.42 | 5.2 |
| 10 | 0.21 | 2.6 |

The 2.1 mg chloride per gm sample (0.21%) is equivalent to 97.3% removal.

EXAMPLE 3

Into a one-liter round bottom flask equipped with mechanical stirrer, thermometer, dropping funnel and Dean-Stark trap with a condenser is added 442 g (0.88 mole at 88% purity) of ALIQUAT® 336 quaternary ammonium salt, 160 g toluene, 100 ml water and 83 ml of 85% $H_3PO_4$ (1.5 mole). The mixture is heated to reflux with stirring. Aliquots of 20 ml of aqueous are withdrawn from the trap and titrated for acid content. At the same time, 20 ml portions of water are added to the reaction to maintain the water level in the reaction. The concentration of HCl in the distilled aqueous phase decreases as the reaction progresses. When the distilled HCl concentration falls to 5% of its initial value, the reaction is cooled, washed twice with water, and the solvent and residual water stripped under vacuum to produce product containing a mixture of the quaternary ammonium mono-hydrogen and dihydrogen phosphate. Following these steps should result in a quaternary ammonium dihydrogen phosphate salt.

EXAMPLE 4

100 ml of a 0.5 molar solution of ALIQUAT® 336 bisulfate salt in toluene is mixed for two minutes with 100 ml of a 1M NaOH solution. The separated aqueous is discarded, and the organic phase is mixed for two more minutes with 100 ml fresh 1M NaOH solution. This is repeated for a third contact and the aqueous separated, which should provide a toluene solution of the quaternary ammonium hydroxide.

What is claimed is:

1. A process for making a quaternary ammonium dihydrogen phosphate or bisulfate salt comprising the steps of: (1) forming a first mixture by contacting a quaternary ammonium halide with: (a) a water-insoluble organic solvent capable of forming a ternary azeotrope with water and hydrogen halide and (b) an amount of water and sulfuric acid or phosphoric acid sufficient to maintain the temperature of the first mixture in the range of from about 98° C. to about 105° C. when heated; (2) heating the first mixture to a temperature sufficient to separate a ternary azeotrope comprised of hydrogen halide, water and the water-insoluble organic solvent from the first mixture to form a second mixture comprised of water, sulfuric acid or phosphoric acid, the water-insoluble organic solvent and a quaternary ammonium dihydrogen phosphate or bisulfate salt.

2. The process of claim 1 wherein the organic solvent is benzene, toluene, heptane, octane or mixtures thereof.

3. The process of claim 1 wherein the organic solvent is toluene.

4. The process of claim 1 wherein the quaternary ammonium halide is a quaternary ammonium fluoride, chloride, bromide or iodide.

5. The process of claim 1 wherein the quaternary ammonium halide is a quaternary ammonium chloride.

6. The process of claim 1 wherein the quaternary ammonium halide is a methyl tri-alkylammonium halide.

7. The process of claim 1 further comprising the step of separating the quaternary ammonium bisulfate salt from the second mixture.

8. A process for making a tri-$C_{8-10}$ alkyl methyl quaternary ammonium bisulfate comprising the steps of: (1) forming a first mixture by contacting a tri-$C_{8-10}$ alkyl methyl quaternary ammonium chloride with: (a) toluene and (b) an amount of water and sulfuric acid sufficient to maintain the temperature of the first mixture in the range of from about 98° C. to about 102° C. when heated; (2) heating the first mixture to a temperature sufficient to separate a ternary azeotrope comprised of hydrogen chloride, water and toluene from the first mixture to form a second mixture comprised of water, sulfuric acid, toluene and a tri-$C_{8-10}$ alkyl methyl quaternary ammonium bisulfate.

9. A liquid quaternary ammonium dihydrogen phosphate or bisulfate salt having a chloride content of less than about one mole percent.

10. The salt of claim 9 wherein the quaternary ammonium salt is a methyl trialkyl ammonium dihydrogen phosphate or bisulfate salt.

11. A method for making a quaternary ammonium salt of the formula

QG wherein Q is $R_1 R_2 R_3 R_4N^+$ and wherein each of $R_1 R_2 R_3 R_4$ is independently an alkyl or cycloalkyl group having from 1 to 22 carbon atoms and G is selected from the group consisting of hydroxide, carbonate, nitrate, chromate, dichromate, vanadate and tungstate comprising the steps of (1) forming a first mixture by contacting a quaternary ammonium halide with: (a) a water-insoluble organic solvent capable of forming a ternary azeotrope with water and hydrogen halide and (b) an amount of water and sulfuric acid or phosphoric acid sufficient to maintain the temperature of the first mixture in the range of from about 98° C. to about 105° C. when heated; (2) heating the first mixture to a temperature sufficient to separate a ternary azeotrope comprised of hydrogen halide, water and the water-insoluble organic solvent from the first mixture to form a second mixture comprised of water, sulfuric acid or phosphoric acid, the water-insoluble organic solvent and a quaternary ammonium dihydrogen phosphate or bisulfate salt; (3) reacting the quaternary ammonium dihydrogen phosphate or bisulfate salt with an aqueous solution of a salt of anion G.

* * * * *